(12) United States Patent
Dahiyat et al.

(10) Patent No.: US 6,403,312 B1
(45) Date of Patent: Jun. 11, 2002

(54) PROTEIN DESIGN AUTOMATIC FOR PROTEIN LIBRARIES

(75) Inventors: Bassil I. Dahiyat, Los Angeles; Robert J. Hayes, Altadena; Jörg Bentzien, Pasadena, all of CA (US); Klaus M. Fiebig, Frankfurt (DE)

(73) Assignee: Xencor, Monrovia, CA (US)

( * ) Notice: Subject to any disclaimer, the term of this patent is extended or adjusted under 35 U.S.C. 154(b) by 0 days.

(21) Appl. No.: 09/419,351

(22) Filed: Oct. 15, 1999

Related U.S. Application Data

(63) Continuation-in-part of application No. 09/564,961, filed on May 4, 2000.
(60) Provisional application No. 60/104,612, filed on Oct. 16, 1998, provisional application No. 60/132,475, filed on May 4, 1999, provisional application No. 60/158,700, filed on Oct. 8, 1999, and provisional application No. 60/138,156, filed on Jun. 7, 1999.

(51) Int. Cl.[7] .......................... C12Q 1/68; G01N 33/53
(52) U.S. Cl. ............................................. 435/6; 435/7.1
(58) Field of Search ...................... 435/6, 7.2; 530/329

(56) References Cited

U.S. PATENT DOCUMENTS 5,527,681 A * 6/1996 Holmes .......................... 435/6

FOREIGN PATENT DOCUMENTS

| WO | 95/22625 | 8/1995 |
|---|---|---|
| WO | 98/32845 | 7/1998 |
| WO | 98/47089 | 10/1998 |
| WO | 00/68396 | 11/2000 |

OTHER PUBLICATIONS

Bowie et al., "A Method to Identify Protein Sequences that Fold into a Known Three–Dimensional Structure," *Science* 253:164–170 (1991).
Dahiyat and Mayo, "Protein Design automation", *Protein Science* 5:895–903 (1996).
Dahiyat and Mayo, "De Novo Protein Design: Fully Automated Sequence Selection," *Science* 278:82–87 (1997).
Desjarlais and Handel, "De novo design of the hydrophobic cores of protein", *Protein Science* 4:2006–2018 (1995).
Harbury et al., "Repacking protein cores with backbone freedom: Structure prediction for coiled coils", *Proc. Natl. Acad. Sci.* USA 92:8408–8412 (1995).
Kono and Doi, "Energy Minimization Method Using Automata Network for Sequence and Side–Chain Conformation Prediction From Given Backbone Geometry", *Proteins: Structure, Function and Genetics* 19:244–255 (1994).
Hellinga, et al., "Optimal sequence selection in proteins of known structure by simulated evolution", *Proc. Natl. Acad. Sci., USA* vol.91:5803–5807 (1994).
Jones, "De novo protein design using pairwise potentials and a genetic algorith",*Protein Science* 3:567–574 (1994).
Lam et al. Application of combinatorial library methods in cance research and drug discovery. Anti–Cancer Drug Design. 12:145–167.*
Gallop et al. Applications of combinatorial technologies to drug discoveries. Background and peptide combinatorial libraries. J. M. Chem. 37:1233–1251. 1994.*

* cited by examiner

*Primary Examiner*—Jyothsna Venkat
*Assistant Examiner*—Barba M. Koroma
(74) *Attorney, Agent, or Firm*—Robin M. Silva; Renee M. Kosslak; Flehr Hohbach Test Albritton & Herbert LLP

(57) ABSTRACT

The invention relates to the use of protein design automaton (PDA) to generate computationally prescreened secondary libraries of proteins, and to methods and compositions utilizing the libraries.

8 Claims, 3 Drawing Sheets

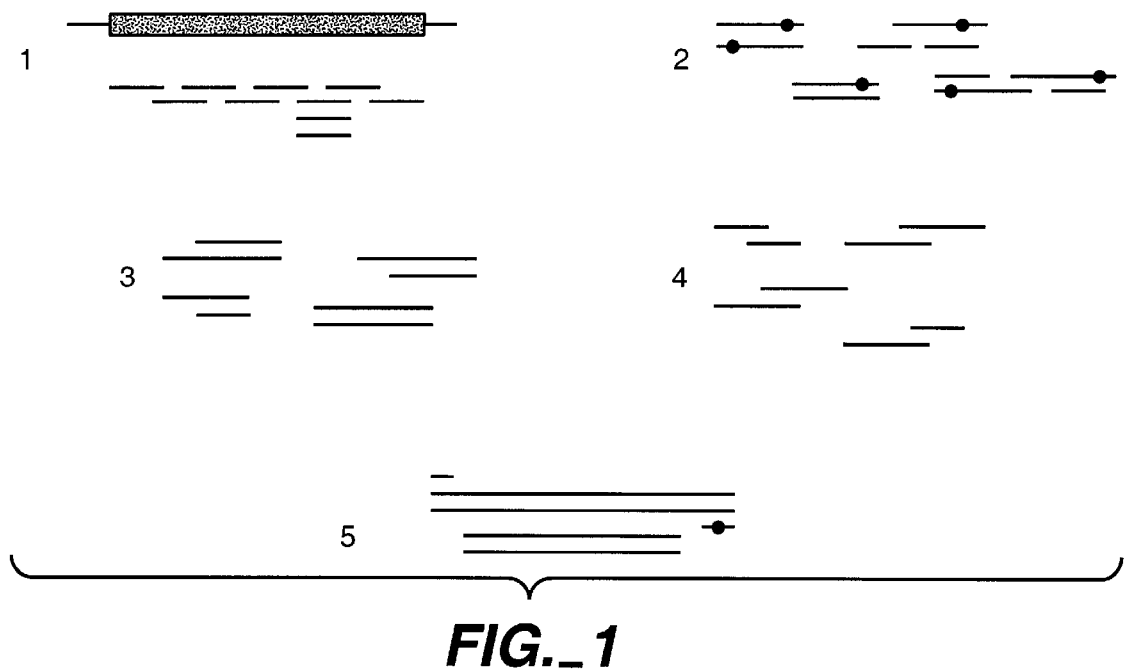
FIG._1
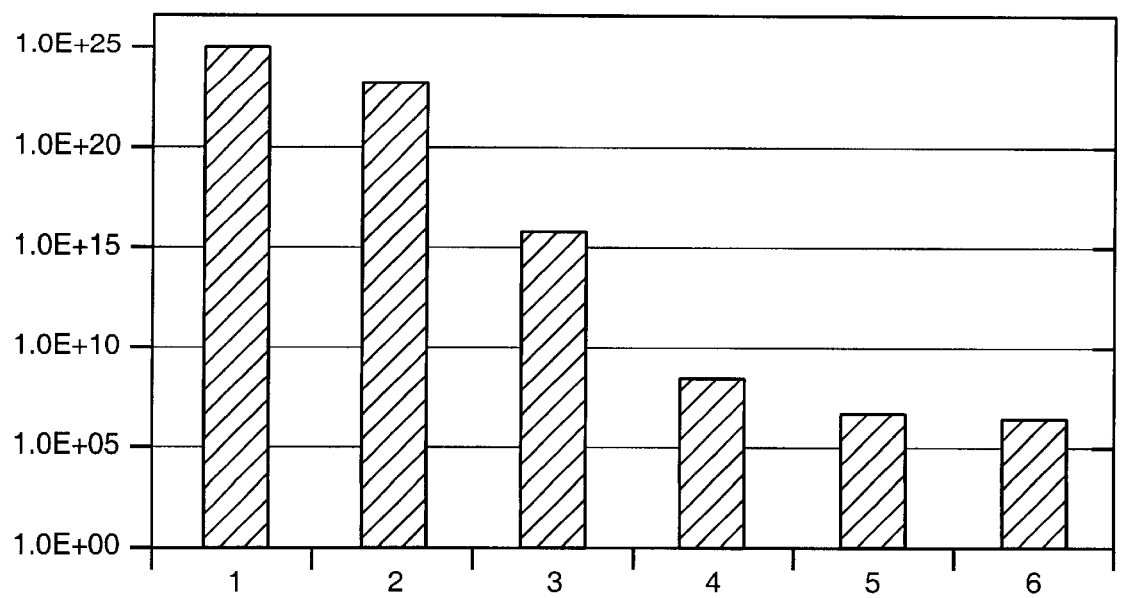
FIG._2

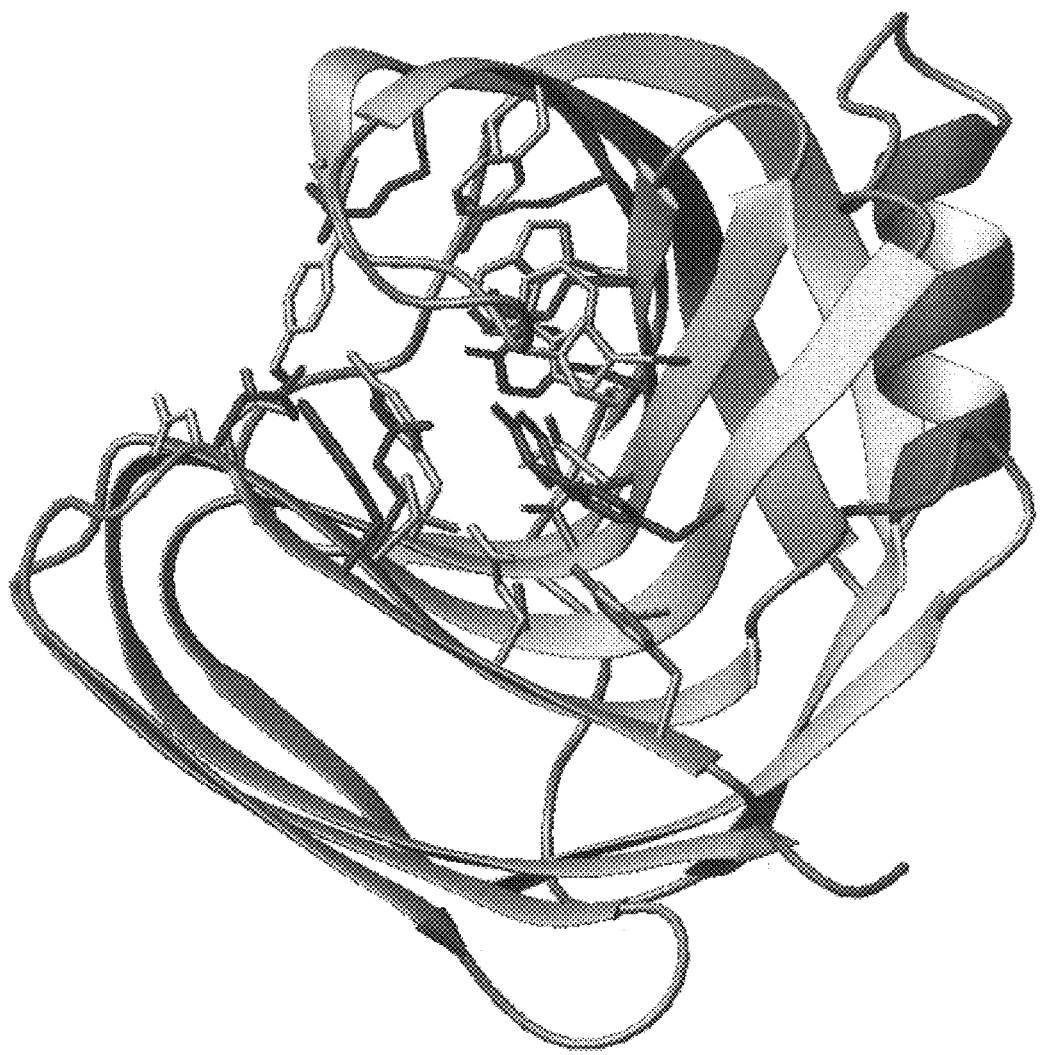
FIG._3

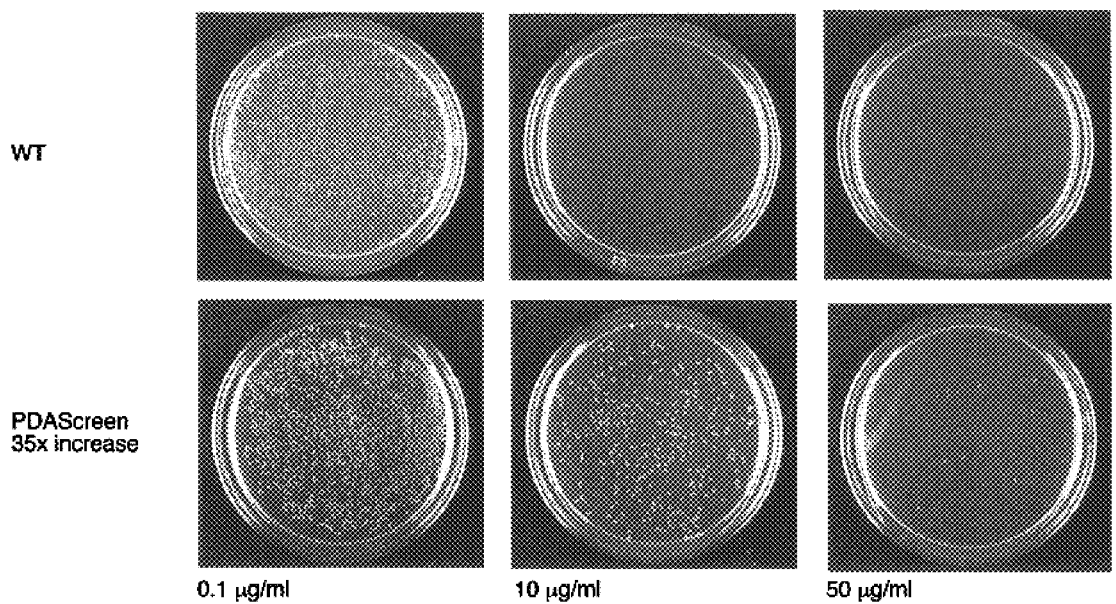
FIG._4

PROTEIN DESIGN AUTOMATIC FOR PROTEIN LIBRARIES

This application is a continuation in part of Ser. No. 60/104,612 filed Oct. 16, 1998. This application claims benefit of Ser. No. 60/132,475 filed May 4, 1999, which claims benefit of Ser. No. 60/158,700 filed Oct. 8, 1999, which claims benefit of Ser. No. 60/138,156 filed Jun. 7, 1999 which is a CIP of Ser. No. 09/564,961 filed May 4, 2000.

FIELD OF THE INVENTION

The invention relates to the use of protein design automation (PDA) to generate computationally prescreened secondary libraries of proteins, and to methods and compositions utilizing the libraries.

BACKGROUND OF THE INVENTION

Directed molecular evolution can be used to create proteins and enzymes with novel functions and properties. Starting with a known natural protein, several rounds of mutagenesis, functional screening, and propagation of successful sequences are performed. The advantage of this process is that it can be used to rapidly evolve any protein without knowledge of its structure. Several different mutagenesis strategies exist, including point mutagenesis by error-prone PCR, cassette mutagenesis, and DNA shuffling. These techniques have had many successes; however, they are all handicapped by their inability to produce more than a tiny fraction of the potential changes. For example, there are $20^{500}$ possible amino acid changes for an average protein approximately 500 amino acids long. Clearly, the mutagenesis and functional screening of so many mutants is impossible; directed evolution provides a very sparse sampling of the possible sequences and hence examines only a small portion of possible improved proteins, typically point mutants or recombinations of existing sequences. By sampling randomly from the vast number of possible sequences, directed evolution is unbiased and broadly applicable, but inherently inefficient because it ignores all structural and biophysical knowledge of proteins.

In contrast, computational methods can be used to screen enormous sequence libraries (up to $10^{80}$ in a single calculation) overcoming the key limitation of experimental library screening methods such as directed molecular evolution. There are a wide variety of methods known for generating and evaluating sequences. These include, but are not limited to, sequence profiling (Bowie and Eisenberg, Science 253(5016): 164–70, (1991)), rotamer library selections (Dahiyat and Mayo, Protein Sci 5(5): 895–903 (1996); Dahiyat and Mayo, Science 278(5335): 82–7 (1997); Desjarlais and Handel, Protein Science 4: 2006–2018 (1995); Harbury et al, PNAS USA 92(18): 8408–8412 (1995); Kono et al., Proteins: Structure, Function and Genetics 19: 244–255 (1994); Hellinga and Richards, PNAS USA 91: 5803–5807 (1994)); and residue pair potentials (Jones, Protein Science 3: 567–574, (1994)).

In particular, U.S. Ser. Nos. 60/061,097, 60/043,464, 60/054,678, 09/127,926 and PCT US98/07254 describe a method termed "Protein Design Automation", or PDA, that utilizes a number of scoring functions to evaluate sequence stability.

It is an object of the present invention to provide computational methods for prescreening sequence libraries to generate and select secondary libraries, which can then be made and evaluated experimentally.

SUMMARY OF THE INVENTION

In accordance with the objects outlined above, the present invention provides methods for generating a secondary library of scaffold protein variants comprising providing a primary library comprising a rank-ordered list of scaffold protein primary variant sequences. A list of primary variant positions in the primary library is then generated, and a plurality of the primary variant positions is then combined to generate a secondary library of secondary sequences.

In an additional aspect, the invention provides methods for generating a secondary library of scaffold protein variants comprising providing a primary library comprising a rank-ordered list of scaffold protein primary variant sequences, and generating a probability distribution of amino acid residues in a plurality of variant positions. The plurality of the amino acid residues is combined to generate a secondary library of secondary sequences. These sequences may then be optionally synthesized and tested, in a variety of ways, including multiplexing PCR with pooled oligonucleotides, error prone PCR, gene shuffling, etc.

In a further aspect, the invention provides compositions comprising a plurality of secondary variant proteins or nucleic acids encoding the proteins, wherein the plurality comprises all or a subset of the secondary library. The invention further provides cells comprising the library, particularly mammalian cells.

In an additional aspect, the invention provides methods for generating a secondary library of scaffold protein variants comprising providing a first library rank-ordered list of scaffold protein primary variants;

generating a probability distribution of amino acid residues in a plurality of variant positions; and synthesizing a plurality of scaffold protein secondary variants comprising a plurality of the amino acid residues to form a secondary library. At least one of the secondary variants is different from the primary variants.

In an additional embodiment, the present invention provides methods executed by a computer under the control of a program, the computer including a memory for storing the program. The method comprising the steps of receiving a protein backbone structure with variable residue positions, establishing a group of potential rotamers for each of the variable residue positions, and analyzing the interaction of each of the rotamers with all or part of the remainder of the protein backbone structure to generate a set of optimized protein sequences. The methods further comprise classifying each variable residue position as either a core, surface or boundary residue. The analyzing step may include a Dead-End Elimination (DEE) computation. Generally, the analyzing step includes the use of at least one scoring function selected from the group consisting of a Van der Waals potential scoring function, a hydrogen bond potential scoring function, an atomic salvation scoring function, a secondary structure propensity scoring function and an electrostatic scoring function. The methods further comprise altering the protein backbone prior to the analysis, comprising altering at least one supersecondary structure parameter value. The methods may further comprise generating a rank ordered list of additional optimal sequences from the globally optimal protein sequence. Some or all of the protein sequences from the ordered list may be tested to produce potential energy test results. The methods may further comprise generating a secondary library and/or ranking a secondary library, using the techniques outlined herein. Thus devices comprising the computer code for running the programs are provided as well.

BRIEF DESCRIPTION OF THE DRAWINGS

FIG. 1 depicts the synthesis of a full-length gene and all possible mutations by PCR. Overlapping oligonucleotides corresponding to the full-length gene (black bar, Step 1) are synthesized, heated and annealed. Addition of Pfu DNA polymerase to the annealed oligonucleotides results in the 5'→3' synthesis of DNA (Step 2) to produce longer DNA fragments (Step 3). Repeated cycles of heating, annealing (Step 4) results in the production of longer DNA, including some full-length molecules. These can be selected by a second round of PCR using primers (arrowed) corresponding to the end of the full-length gene (Step 5).

FIG. 2 depicts the reduction of the dimensionality of sequence space by PDA screening. From left to right, 1: without PDA; 2: without PDA not counting Cysteine, Proline, Glycine; 3: with PDA using the 5 1% criterion, modeling free enzyme; 4: with PDA using the 1% criterion, modeling enzyme-substrate complex; 5: with PDA using the 5% criterion modeling free enzyme; 6: with PDA using the 5% criterion modeling enzyme-substrate complex.

FIG. 3 depicts the active site of *B. circulans xylanase*. Those positions included in the PDA design are shown by their side chain representation. In red are wild type residues (their conformation was allowed to change, but not their amino acid identity). In green are positions whose conformation and identity were allowed to change (to any amino acid except proline, cysteine and glycine).

FIG. 4 depicts cefotaxime resistance of *E. coli* expressing wild type (WT) and PDA Screened β-lactamase; results shown for increasing concentrations of cefotaxime.

DETAILED DESCRIPTION OF THE INVENTION

The present invention is directed to methods of using computational screening of protein sequence libraries (that can comprise up to $10^{80}$ or more members) to select smaller secondary libraries of protein sequences (that can comprise up to $10^{13}$ members), that can then be actually synthesized and experimentally tested in the desired assay, for improved function and properties.

The invention has two broad uses; first, the invention can be used to prescreen libraries based on known scaffold proteins. That is, computational screening for stability (or other properties) may be done on either the entire protein or some subset of residues, as desired and described below. By using computational methods to generate a threshold or cutoff to eliminate disfavored sequences, the percentage of useful variants in a given variant set size can increase, and the required experimental outlay is decreased.

In addition, the present invention finds use in the screening of random peptide libraries. As is known, signaling pathways in cells often begin with an effector stimulus that leads to a phenotypically describable change in cellular physiology. Despite the key role intracellular signaling pathways play in disease pathogenesis, in most cases, little is understood about a signaling pathway other than the initial stimulus and the ultimate cellular response.

Historically, signal transduction has been analyzed by biochemistry or genetics. The biochemical approach dissects a pathway in a "stepping-stone" fashion: find a molecule that acts at, or is involved in, one end of the pathway, isolate assayable quantities and then try to determine the next molecule in the pathway, either upstream or downstream of the isolated one. The genetic approach is classically a "shot in the dark": induce or derive mutants in a signaling pathway and map the locus by genetic crosses or complement the mutation with a cDNA library. Limitations of biochemical approaches include a reliance on a significant amount of pre-existing knowledge about the constituents under study and the need to carry such studies out in vitro, post-mortem. Limitations of purely genetic approaches include the need to first derive and then characterize the pathway before proceeding with identifying and cloning the gene.

Screening molecular libraries of chemical compounds for drugs that regulate signal systems has led to important discoveries of great clinical significance. Cyclosporin A (CsA) and FK506, for examples, were selected in standard pharmaceutical screens for inhibition of T-cell activation. It is noteworthy that while these two drugs bind completely different cellular proteins—cyclophilin and FK506 binding protein (FKBP), respectively, the effect of either drug is virtually the same—profound and specific suppression of T-cell activation, phenotypically observable in T cells as inhibition of mRNA production dependent on transcription factors such as NF-AT and NF-κB. Libraries of small peptides have also been successfully screened in vitro in assays for bioactivity. The literature is replete with examples of small peptides capable of modulating a wide variety of signaling pathways. For example, a peptide derived from the HIV-1 envelope protein has been shown to block the action of cellular calmodulin.

Accordingly, generation of random or semi-random sequence libraries of proteins and peptides allows for the selection of proteins (including peptides, oligopeptides and polypeptides) with useful properties. The sequences in these experimental libraries can be randomized at specific sites only, or throughout the sequence. The number of sequences that can be searched in these libraries grows exponentially with the number of positions that are randomized. Generally, only up to $10^{12}$–$10^{15}$ sequences can be contained in a library because of the physical constraints of laboratories (the size of the instruments, the cost of producing large numbers of biopolymers, etc.). Other practical considerations can often limit the size of the libraries to $10^6$ or fewer. These limits are reached for only 10 amino acid positions. Therefore, only a sparse sampling of sequences is possible in the search for improved proteins or peptides in experimental sequence libraries, lowering the chance of success and almost certainly missing desirable candidates. Because of the randomness of the changes in these sequences, most of the candidates in the library are not suitable, resulting in a waste of most of the effort in producing the library.

However, using the automated protein design techniques outlined below, virtual libraries of protein sequences can be generated that are vastly larger than experimental libraries. Up to $10^{80}$ candidate sequences can be screened computationally and those that meet design criteria which favor stable and functional proteins can be readily selected. An experimental library consisting of the favorable candidates found in the virtual library screening can then be generated, resulting in a much more efficient use of the experimental library and overcoming the limitations of random protein libraries.

Two principle benefits come from the virtual library screening: (1) the automated protein design generates a list of sequence candidates that are favored to meet design criteria; it also shows which positions in the sequence are readily changed and which positions are unlikely to change without disrupting protein stability and function. An experimental random library can be generated that is only randomized at the readily changeable, non-disruptive sequence positions. (2) The diversity of amino acids at these positions can be limited to those that the automated design shows are compatible with these positions. Thus, by limiting the number of randomized positions and the number of possibilities at these positions, the number of wasted sequences produced in the experimental library is reduced, thereby increasing the probability of success in finding sequences with useful properties.

In addition, by computationally screening very large libraries of mutants, greater diversity of protein sequences can be screened, leading to greater improvements in protein function. Further, fewer mutants need to be tested experimentally to screen a given library size, reducing the cost and difficulty of protein engineering. By using computational methods to pre-screen a protein library, the computational features of speed and efficiency are combined with the ability of experimental library screening to create new activities in proteins for which appropriate computational models and structure-function relationships are unclear.

Similarly, novel methods to create secondary libraries derived from very large computational mutant libraries allow the rapid testing of large numbers of computationally designed sequences.

In addition, as is more fully outlined below, the libraries may be biased in any number of ways, allowing the generation of secondary libraries that vary in their focus; for example, domains, subsets of residues, active or binding sites, surface residues, etc., may all be varied or kept constant as desired.

Accordingly, the present invention provides methods for generating secondary libraries of scaffold protein variants. By "protein" herein is meant at least two amino acids linked together by a peptide bond. As used herein, protein includes proteins, oligopeptides and peptides. The peptidyl group may comprise naturally occurring amino acids and peptide bonds, or synthetic peptidomimetic structures, i.e. "analogs", such as peptoids (see Simon et al., *PNAS USA* 89(20):9367 (1992)). The amino acids may either be naturally occuring or non-naturally occuring; as will be appreciated by those in the art, any structure for which a set of rotamers is known or can be generated can be used as an amino acid. The side chains may be in either the (R) or the (S) configuration. In a preferred embodiment, the amino acids are in the (S) or L-configuration.

The scaffold protein may be any protein for which a three dimensional structure is known or can be generated; that is, for which there are three dimensional coordinates for each atom of the protein. Generally this can be determined using X-ray crystallographic techniques, NMR techniques, de novo modelling, homology modelling, etc. In general, if X-ray structures are used, structures at 2 Å resolution or better are preferred, but not required.

The scaffold proteins may be from any organism, including prokaryotes and eukaryotes, with enzymes from bacteria, fungi, extremeophiles such as the archebacteria, insects, fish, animals (particularly mammals and particularly human) and birds all possible.

Thus, by "scaffold protein" herein is meant a protein for which a secondary library of variants is desired. As will be appreciated by those in the art, any number of scaffold proteins find use in the present invention. Specifically included within the definition of "protein" are fragments and domains of known proteins, including functional domains such as enzymatic domains, binding domains, etc., and smaller fragments, such as turns, loops, etc. That is, portions of proteins may be used as well. In addition, "protein" as used herein includes proteins, oligopeptides and peptides. In addition, protein variants, i.e. non-naturally occuring protein analog structures, may be used.

Suitable proteins include, but are not limited to, industrial and pharmaceutical proteins, including ligands, cell surface receptors, antigens, antibodies, cytokines, hormones, transcription factors, signaling modules, cytoskeletal proteins and enzymes. Suitable classes of enzymes include, but are not limited to, hydrolases such as proteases, carbohydrases, lipases; isomerases such as racemases, epimerases, tautomerases, or mutases; transferases, kinases, oxidoreductases, and phophatases. Suitable enzymes are listed in the Swiss-Prot enzyme database. Suitable protein backbones include, but are not limited to, all of those found in the protein data base compiled and serviced by the Research Collaboratory for Structural Bioinformatics (RCSB, formerly the Brookhaven National Lab).

Specifically, preferred scaffold proteins include, but are not limited to, those with known structures (including variants) including cytokines (IL-1ra (+receptor complex), IL-1 (receptor alone), IL-1a, IL-1b (including variants and or receptor complex), IL-2, IL-3, IL-4, IL-5, IL6, IL-8, IL-10, IFN-β, INF-γ, IFN-α-2a; IFN-α-2B, TNF-α; CD40 ligand (chk), Human Obesity Protein Leptin, Granulocyte-Macrophage Colony-Stimulating Factor, Bone Morphogenetic Protein-7, Ciliary Neurotrophic Factor, Granulocyte-Macrophage Colony-Stimulating Factor, Monocyte Chemoattractant Protein 1, Macrophage Migration Inhibitory Factor, Human Glycosylation-Inhibiting Factor, Human Rantes, Human Macrophage Inflammatory Protein 1 Beta, human growth hormone, Leukemia Inhibitory Factor, Human Melanoma Growth Stimulatory Activity, neutrophil activating peptide-2, Cc-Chemokine Mcp-3, Platelet Factor M2, Neutrophil Activating Peptide 2, Eotaxin, Stromal Cell-Derived Factor-1, Insulin, Insulin-like Growth Factor I, Insulin-like Growth Factor II, Transforming Growth Factor B1, Transforming Growth Factor B2, Transforming Growth Factor B3, Transforming Growth Factor A, Vascular Endothelial growth factor (VEGF), acidic Fibroblast growth factor, basic Fibroblast growth factor, Endothelial growth factor, Nerve growth factor, Brain Derived Neurotrophic Factor, Ciliary Neurotrophic Factor, Platelet Derived Growth Factor, Human Hepatocyte Growth Factor, Glial Cell-Derived Neurotrophic Factor, (as well as the 55 cytokines in PDB Jan. 12, 1999. Erythropoietin; other extracellular signaling moieties, including, but not limited to, hedgehog Sonic, hedgehog Desert, hedgehog Indian, hCG; coaguation factors including, but not limited to, TPA and Factor VIIa; transcription factors, including but not limited to, p53, p53 tetramerization domain, Zn fingers (of which more than 12 have structures), homeodomains (of which 8 have structures), leucine zippers (of which 4 have structures); antibodies, including, but not limited to, cFv; viral proteins, including, but not limited to, hemagglutinin trimerization domain and hiv Gp41 ectodomain (fusion domain); intracellular signaling modules, including, but not limited to, SH2 domains (of which 8 structures are known), SH3 domains (of which 11 have structures), and Pleckstin Homology Domains; receptors, including, but not limited to, the extracellular Region Of Human Tissue Factor Cytokine-Binding Region Of Gp130, G-CSF receptor, erythropoietin receptor, Fibroblast Growth Factor receptor, TNF receptor, IL-1 receptor, IL-1 receptor/IL1ra complex, IL4 receptor, INF-γ receptor alpha chain, MHC Class I, MHC Class II, T Cell Receptor, Insulin receptor, insulin receptor tyrosine kinase and human growth hormone receptor.

Once a scaffold protein is chosen, a primary library is generated using computational processing. Generally speaking, the goal of the computational processing is to determine a set of optimized protein sequences. By "optimized protein sequence" herein is meant a sequence that best fits the mathematical equations of the computational process. As will be appreciated by those in the art, a global optimized sequence is the one sequence that best fits the equations (for example, when PDA is used, the global optimzed sequence is the sequence that best fits Equation 1, below); i.e. the sequence that has the lowest energy of any possible sequence. However, there are any number of sequences that are not the global minimum but that have low energies.

Thus, a "primary library" as used herein is a collection of optimized sequences, generally in the form of a rank-ordered list. In theory, all possible sequences of a protein may be ranked; however, currently $10^{13}$ sequences is a practical limit. Thus, in general, some subset of all possible sequences is used as the primary library; generally, the top $10^3$ to $10^{13}$ sequences are chosen as the primary library. The cutoff for inclusion in the rank ordered list of the primary library can be done in a variety of ways. For example, the cutoff may be just an arbitrary exclusion point: the top 1 sequences may comprise the primary library. Alternatively, all sequences scoring within a certain limit of the global optimum can be used; for example, all sequences with 10 kcal/mol of the global optimum could be used as the primary library. This method has the advantage of using a direct measure of fidelity to a three dimensional structure to determine inclusion. This approach can be used to insure that library mutations are not limited to positions that have the lowest energy gap between different mutations. Alternatively, the cutoff may be enforced when a predetermined number of mutations per position is reached. As a rank ordered sequence list is lengthened and the library is enlarged, more mutations per position are defined. Alternatively, the total number of sequences defined by the recombination of all mutations can be used as a cutoff criterion for the primary sequence library. Preferred values for the total number of sequences range from 100 to $10^{20}$, particularly preferred values range from 1000 to $10^{13}$, especially preferred values range from 1000 to $10^7$. Alternatively, the first occurrence in the list of predefined undesirable residues can be used as a cutoff criterion. For example, the first hydrophilic residue occurring in a core position would limit the list. It should also be noted that while these methods are described in conjunction with limiting the size of the primary library, these same techniques may be used to formulate the cutoff for inclusion in the secondary library as well.

Thus, the present invention provides methods to generate a primary library comprising a rank ordered list of sequences, generally in terms of theoretical quantitative stability, as is more fully described below. Generating a primary library to optimize the stability of a conformation can be used to stabilize the active site conformation of an enzyme, which will improve its activity. Similarly, stabilizing a ligand-receptor complex or enzyme-substrate complex will improve the binding affinity.

The primary libraries can be generated in a variety of ways. In essence, any methods that can result in the relative ranking of the possible sequences of a protein based on measurable stability parameters can be used. As will be appreciated by those in the art, any of the methods described herein or known in the art may be used alone, or in combination with other methods.

In a preferred embodiment, the scaffold protein is an enzyme and highly accurate electrostatic models can be used for enzyme active site residue scoring to improve enzyme active site libraries (see Warshel, *Computer Modeling of Chemical Reactions in Enzymes and Solutions*, Wiley & Sons, New York, (1991), hereby expressly incorporated by reference). These accurate models can assess the relative energies of sequences with high precision, but are computationally intensive.

Similarly, molecular dynamics calculations can be used to computationally screen sequences by individually calculating mutant sequence scores and compiling a rank ordered list.

In a preferred embodiment, residue pair potentials can be used to score sequences (Miyazawa et al., Macromolecules 18(3):534–552 (1985), expressly incorporated by reference) during computational screening.

In a preferred embodiment, sequence profile scores (Bowie et al., Science 253(5016):164–70 (1991), incorporated by reference) and/or potentials of mean force (Hendlich et al., J. Mol. Biol. 216(1):167–180 (1990), also incorporated by reference) can also be calculated to score sequences. These methods assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1–8 (1998), hereby expressly incorporated by reference). Similarly, scoring functions can be used to screen for sequences that would create disulfide bonds in the protein. These potentials attempt to specifically modify a protein structure to introduce a new structural motif.

In addition, sequence and/or structural alignment programs can be used to generate primary libraries. For example, structural alignment of structurally related proteins can be done to generate sequence alignments (Orengo et al., Structure 5(8):1093–108 (1997); Holm et al., Nucleic Acid Res. 26(1): 316–9 (1998), both of which are incorporated by reference). These sequence alignments can then be examined to determine the observed sequence variations.

Similarly, sequence homology based alignment methods can be used to create sequence alignments of proteins related to the target structure (Altschul et al., J. Mol. Biol. 215(3):403 (1990), incorporated by reference). These sequence alignments are then examined to determine the observed sequence variations. These sequence variations are tabulated to define a primary library.

These sequence variations can be tabulated and a secondary library defined from them as defined below. Alternatively, the allowed sequence variations can be used to define the amino acids considered at each position during the computational screening. Another variation is to bias the score for amino acids that occur in the sequence alignment, thereby increasing the likelihood that they are found during computational screening but still allowing consideration of other amino acids. This bias would result in a focused primary library but would not eliminate from consideration amino acids not found in the alignment.

Similarly, as outlined above, other computational methods are known, including, but not limited to, sequence profiling (Bowie and Eisenberg, Science 253(5016): 164–70, (1991)), rotamer library selections (Dahiyat and Mayo, Protein Sci 5(5): 895–903 (1996); Dahiyat and Mayo, Science 278(5335): 82–7 (1997); Desjarlais and Handel, Protein Science 4: 2006–2018 (1995); Harbury PNAS USA 92(18): 8408–8412 (1995); Kono et al., Proteins: Structure, Function and Genetics 19: 244–255 (1994); Hellinga and Richards, PNAS USA 91: 5803–5807 (1994)); and residue pair potentials (Jones, Protein Science 3: 567–574, (1994)), all of which are expressly incorporated by reference.

In a preferred embodiment, the computational method used to generate the primary library is Protein Design Automation (PDA), as is described in U.S. Ser. Nos. 60/061,097, 60/043,464, 60/054,678, 09/127,926, U.S. Pat. No. 6,269,312 and PCT US98/07254, all of which are expressly incorporated herein by reference. Briefly, PDA can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated.

As outlined in U.S. Ser. No. 09/127,926, U.S. Pat. No. 6,269,312 the protein backbone (comprising (for a naturally occuring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization (Mayo et al., *J. Phys. Chem.* 94:8897 (1990)) of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occuring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues. For example, residues which are known to be important for biological activity, such as the residues which form the active site of an enzyme, the substrate binding site of an enzyme, the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc.

In a preferred embodiment, each variable position is classified as either a core, surface or boundary residue position, although in some cases, as explained below, the variable position may be set to glycine to minimize backbone strain. Any combination of core, surface and boundary positions can be utilized: core, surface and boundary residues; core and surface residues; core and boundary residues, and surface and boundary residues, as well as core residues alone, surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modelling. Alternatively, a preferred embodiment utilizes an assessment of the orientation of the Cα-Cβ vectors relative to a solvent accessible surface computed using only the template Cα atoms, as outlined in U.S. Ser. Nos. 60/061,097, 60/043,464, 60/054,678, 09/127,926, U.S. Pat. No. 6,269,312 and PCT US98/07254.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the a scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occuring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0°, the position is set to glycine to minimize backbone strain.

Once the group of potential rotamers is assigned for each variable residue position, processing proceeds as outlined in U.S. Ser. No. 09/127,926, U.S. Pat. No. 6,269,312 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1

$$E_{total} = nE_{vdw} + nE_{as} + nE_{h-bonding} + nE_{ss} + nE_{elec} \qquad \text{Equation 1}$$

In Equation 1, the total energy is the sum of the energy of the van der Waals potential ($E_{vdw}$), the energy of atomic solvation ($E_{as}$), the energy of hydrogen bonding ($E_{h-bonding}$), the energy of secondary structure ($E_{ss}$) and the energy of electrostatic interaction ($E_{elec}$). The term n is either 0 or 1, depending on whether the term is to be considered for the particular residue position.

As outlined in U.S. Ser. Nos. 60/061,097, 60/043,464, 60/054,678, 09/127,926, U.S. Pat. No. 6,269,312 and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer 10 with the entire remainder of the protein, i.e. both the entire template and all other rotamers, is done. However, as outlined above, it is possible to only model a portion of a protein, for example a domain of a larger protein, and thus in some cases, not all of the protein need be considered.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic salvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

Once the singles and doubles energies are calculated and stored, the next step of the computational processing may occur. As outlined in U.S. Ser. No. 7,926, U.S. Pat. No. 6,296,312 a PCT US98/0725 4, preferred embodiments utilize a Dead End Elimination (DEE) step, and preferably a Monte Carlo step.

The computational processing results in a set of optimized protein sequences. These optimized protein sequences are generally, but not always, significantly different from the wild-type sequence from which the backbone was taken. That is, each optimized protein sequence preferably comprises at least about 5–10% variant amino acids from the starting or wild-type sequence, with at least about 15–20% changes being preferred and at least about 30% changes being particularly preferred.

The cutoff for the primary library is then enforced, resulting in a set of primary sequences forming the primary library. As outlined above, this may be done in a variety of ways, including an arbitrary cutoff, an energy limitation, or when a certain number of residue positions have been varied. In general, the size of the primary library will vary with the size of the protein, the number of residues that are changing, the computational methods used, the cutoff applied and the discretion of the user. In general, it is preferable to have the primary library be large enough to randomly sample a reasonable sequence space to allow for robust secondary libraries. Thus, primary libraries that range from about 50 to about $10^{13}$ are preferred, with from about 1000 to about $10^7$ being particularly preferred, and from about 1000 to about 100,000 being especially preferred.

In a preferred embodiment, although this is not required, the primary library comprises the globally optimal sequence in its optimal conformation, i.e. the optimum rotamer at each variable position. That is, computational processing is run until the simulation program converges on a single sequence which is the global optimum. In a preferred embodiment, the primary library comprises at least two optimized protein sequences. Thus for example, the computational processing step may eliminate a number of disfavored combinations but be stopped prior to convergence, providing a library of sequences of which the global optimum is one. In addition, further computational analysis, for example using a different method, may be run on the library, to further eliminate sequences or rank them differently. Alternatively, as is more fully described in U.S. Ser. Nos. 60/061,097, 60/043,464, 60/054,678, 09/127,926, U.S. Pat. No. 6,296,312 and PCT US98/07254, the global optimum may be reached, and then further computational processing may occur, which generates additional optimized sequences in the neighborhood of the global optimum.

In addition, in some embodiments, primary library sequences that did not make the cutoff are included in the primary library. This may be desirable in some situations to evaluate the primary library generation method, to serve as controls or comparisons, or to sample additional sequence space. For example, in a preferred embodiment, the wild-type sequence is included.

It should also be noted that combining different primary libraries may be done. For example, positions in a protein that show a great deal of mutational diversity in computational screening can be fixed as outlined below and a different primary library regenerated. A rank ordered list of the same length as the first would now show diversity in previously rarely changing positions. The variants from the first primary library can be combined with the variants from the second primary library to provide a combined library at lower computational cost than creating a very long rank ordered list. This approach can be particularly useful to sample sequence diversity in both low energy gap, readily changing surface positions and high energy gap, rarely changing core positions.

Thus, the present invention provides primary libraries comprising a rank ordered list of sequences.

In one embodiment, all or a portion of the primary library serves as the secondary library. That is, a cutoff is applied to the primary sequences and these sequences serve as the secondary library, without further manipulation or recombination. The library members can be made as outlined below, e.g. by direct synthesis or by constructing the nucleic acids encoding the library members, expressing them in a suitable host, optionally followed by screening.

In a preferred embodiment, the primary library of the scaffold protein is used to generate a secondary library. As will be appreciated by those in the art, the secondary library can be either a subset of the primary library, or contain new library members, i.e. sequences that are not found in the primary library. That is, in general, the variant positions and/or amino acid residues in the variant positions can be recombined in any number of ways to form a new library that exploits the sequence variations found in the primary library. That is, having identified "hot spots" or important variant positions and/or residues, these positions can be recombined in novel ways to generate novel sequences to form a secondary library. Thus, in a preferred embodiment, the secondary library comprises at least one member sequence that is not found in the primary library, and preferably a plurality of such sequences.

In a preferred embodiment, the secondary library is generated by tabulating the amino acid positions that vary from a reference sequence. The reference sequence can be arbitrarily selected, or preferably is chosen either as the wild-type sequence or the global optimum sequence, with the latter being preferred. That is, each amino acid position that varies in the primary library is tabulated. Of course, if the original computational analysis fixed some positions, the variable positions of the secondary library will comprise either just these original variable positions or some subset of these original variable positions. That is, assuming a protein of 100 amino acids, the original computational screen can allow all 100 positions to be varied. However, due to the cutoff in the primary library, only positions may vary. Alternatively, assuming the same 100 amino acid protein, the original computational screen could have varied only 25 positions, keeping the other 75 fixed; this could result in only 12 of the 25 being varied in the cutoff primary library. These primary library positions can then be recombined to form a secondary library, wherein all possible combinations of these variable positions form the secondary library. It should be noted that the non-variable positions are set to the reference sequence positions.

The formation of the secondary library using this method may be done in two general ways; either all variable positions are allowed to be any amino acid, or subsets of amino acids are allowed for each position.

In a preferred embodiment, all amino acid residues are allowed at each variable position identified in the primary library. That is, once the variable positions are identified, a secondary library comprising every combination of every amino acid at each variable position is made.

In a preferred embodiment, subsets of amino acids are chosen. The subset at any position may be either chosen by the user, or may be a collection of the amino acid residues generated in the primary screen. That is, assuming core residue 25 is variable and the primary screen gives 5 different possible amino acids for this position, the user may chose the set of good core residues outlined above (e.g. hydrophobic residues), or the user may build the set by choosing the 5 different amino acids generated in the primary screen. Alternatively, combinations of these techniques may be used, wherein the set of identified residues is manually expanded. For example, in some embodiments, fewer than the number of amino acid residues is chosen; for example, only three of the five may be chosen. Alternatively, the set is manually expanded; for example, if the computation picks two different hydrophobic residues, additional choices may be added.

In addition, this may be done by analyzing the primary library to determine which amino acid positions in the scaffold protein have a high mutational frequency, and which positions have a low mutation frequency. The secondary library can be generated by randomizing the amino acids at the positions that have high numbers of mutations, while keeping constant the positions that do not have mutations above a certain frequency. For example, if the position has less than 20% and more preferably 10% mutations, it may be kept constant as the reference sequence position.

In a preferred embodiment, a probability distribution table is generated. In this embodiment, the frequency of each amino acid residue at each variable position is identified. Frequencies can be thresholded, wherein any variant frequency lower than a cutoff is set to zero. This cutoff is preferably 1%, 2%, 5%, 10% or 20%, with 10% being particularly preferred. These frequencies are then built into the secondary library. That is, as above, these variable positions are collected and all possible combinations are generated, but the amino acid residues that "fill" the secondary library are utilized on a frequency basis. Thus, in a non-frequency based secondary library, a variable position that has 5 possible residues will have 20% of the proteins comprising that variable position with the first possible residue, 20% with the second, etc. However, in a frequency based secondary library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated, a secondary library created by recombining variable positions and/or residues at the variable position may not be in a rank-ordered list. In some embodiments, the entire list may just be made and tested. Alternatively, in a preferred embodiment, the secondary library is also in the form of a rank ordered list. This may be done for several reasons, including the size of the secondary library is still too big to generate experimentally, or for predictive purposes. This may be done in several ways. In one embodiment, the secondary library is ranked using the scoring functions of PDA to rank the library members. Alternatively, statistical methods could be used. For example, the secondary library may be ranked by frequency score; that is, proteins containing the most of high frequency residues could be ranked higher, etc. This may be done by adding or multiplying the frequency at each variable position to generate a numerical score. Similarly, the secondary library different positions could be weighted and then the proteins scored; for example, those containing certain residues could be arbitrarily ranked.

As outlined herein, secondary libraries can be generated in two general ways. The first is computationally, as above, wherein the primary library is further computationally manipulated, for example by recombining the possible variant positions and/or amino acid residues at each variant position. It may be ranked, as outlined above. This computationally-derived secondary library can then be experimentally generated by synthesizing the library members or nucleic acids encoding them, as is more fully outlined below. Alternatively, the secondary library is made experimentally; that is, nucleic acid recombination techniques are used to experimentally generate the combinations. This can be done in a variety of ways, as outlined below.

In a preferred embodiment, the different protein members of the secondary library may be chemically synthesized. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically. See for example Wilken et al, Curr. Opin. Biotechnol. 9:412–26 (1998), hereby expressly incorporated by reference.

In a preferred embodiment, particularly for longer proteins or proteins for which large samples are desired, the secondary library sequences are used to create nucleic acids such as DNA which encode the member sequences and which can then be cloned into host cells, expressed and assayed, if desired. Thus, nucleic acids, and particularly DNA, can be made which encodes each member protein sequence. This is done using well known procedures. The choice of codons, suitable expression vectors and suitable host cells will vary depending on a number of factors, and can be easily optimized as needed.

In a preferred embodiment, multiple PCR reactions with pooled oligonucleotides is done, as is generally depicted in FIG. 1. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of mutations defined by the secondary library.

In a preferred embodiment, the different oligonucleotides are added in relative amounts corresponding to the probability distribution table. The multiple PCR reactions thus result in full length sequences with the desired combinations of mutations in the desired proportions.

The total number of oligonucleotides needed is a function of the number of positions being mutated and the number of mutations being considered at these positions:

(number of oligos for constant positions)+$M1+M2+M3+\ldots$
$Mn$=(total number of oligos required), where $Mn$ is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being mutated, or for more than one position being mutated. The multiple positions being mutated must be close in sequence to prevent the oligo length from being impractical. For multiple mutating positions on an oligonucleotide, particular combinations of mutations can be included or excluded in the library by including or excluding the oligonucleotide encoding that combination. The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in secondary libraries defining different length proteins, which can be expressed by a library of pooled oligonucleotide of different lengths.

In a preferred embodiment, error-prone PCR is done to generate the secondary library. See U.S. Pat. Nos. 5,605,793, 5,811,238, and 5,830,721, all of which are hereby incorporated by reference. This can be done on the optimal sequence or on top members of the library. In this embodiment, the gene for the optimal sequence found in the computational screen of the primary library can be synthesized. Error prone PCR is then performed on the optimal sequence gene in the presence of oligonucleotides that code for the mutations at the variant positions of the secondary library (bias oligonucleotides). The addition of the oligonucleotides will create a bias favoring the incorporation of the mutations in the secondary library. Alternatively, only oligonucleotides for certain mutations may be used to bias the library.

In a preferred embodiment, gene shuffling with error prone PCR can be performed on the gene for the optimal sequence, in the presence of bias oligonucleotides, to create a DNA sequence library that reflects the proportion of the mutations found in the secondary library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions can be used to generate bias oligonucleotides; random positions may be chosen; a few top scoring and a few low scoring ones may be chosen; etc. What is important is to generate new sequences based on preferred variable positions and sequences.

In a preferred embodiment, a secondary library may be computationally remanipulated to form an additional secondary library. For example, any of the secondary library sequences may be chosen for a second round of PDA, by freezing or fixing some or all of the changed positions in the first secondary library. Alternatively, only changes seen in the last probability distribution table are allowed. Alternatively, the stringency of the probability table may be altered, either by increasing or decreasing the cutoff for inclusion. Similarly, the secondary library may be recombined experimentally after the first round; for example, the best gene/genes from the first screen may be taken and gene assembly redone (using techniques outlined below, multiple PCR, error prone PCR, shuffling, etc.). Alternatively, the fragments from one or more good gene(s) to change probabilities at some positions. This biases the search to an area of sequence space found in the first round of computational and experimental screening.

As outlined herein, any number of protein attributes may be altered in these methods, including, but not limited to, enzyme activity, stability, solubility, aggregation, binding affinity, binding specificity, substrate specificity, structural integrity, immunogenicity, toxicity, generate peptide and peptidomimmetic libraries, create new antibody CDR's, generate new DNA, RNA bindings, etc.

It should be noted that therapeutic proteins utilized in these methods will preferentially have residues in the hydrophobic cores screened, to prevent changes in the molecular surface of the protein that might induce immunogenic responses. Therapeutic proteins can also be designed in the region surrounding their binding sites to their receptors. Such a region can be defined, for example, by including in the design all residues within a certain distance, for example 4.5 Å of the binding site residues. This range can vary from 4 to 6 Å. This design will serve to improve enzyme activity and specificity.

In a preferred embodiment, the methods of the invention are used not on known scaffold proteins, but on random peptides, to search a virtual library for those sequences likely to adapt a stable conformation. As discussed above, there is a current benefit and focus on screening random peptide libraries to find novel binding/modulators. However, the sequences in these experimental libraries can be randomized at specific sites only, or throughout the sequence. The number of sequences that can be searched in these libraries grows expontentially with the number of positions that are randomized. Generally, only up to $10^{12}$–$10^{15}$ sequences can be contained in a library because of the physical constraints of laboratories (the size of the instruments, the cost of producing large numbers of biopolymers, etc.). Other practical considerations can often limit the size of the libraries to $10^6$ or fewer. These limits are reached for only 10 amino acid positions. Therefore, only a sparse sampling of sequences is possible in the search for improved proteins or peptides in experimental sequence libraries, lowering the chance of success and almost certainly missing desirable candidates. Because of the randomness of the changes in these sequences, most of the candidates in the library are not suitable, resulting in a waste of most of the effort in producing the library.

However, using the automated protein design techniques outlined herein, virtual libraries of protein sequences can be generated that are vastly larger than experimental libraries. Up to $10^{75}$ candidate sequences can be screened computationally and those that meet design criteria which favor stable and functional proteins can be readily selected. An experimental library consisting of the favorable candidates found in the virtual library screening can then be generated, resulting in a much more efficient use of the experimental library and overcoming the limitations of random protein libraries. Thus, the methods of the invention allow the virtual screening of a set of random peptides for peptides likely to take on a particular structure, and thus eliminating the large number of unpreferred or unallowed conformations without having to make and test the peptides.

As mentioned above, two principle benefits come from the virtual library screening: (1) the automated protein design generates a list of sequence candidates that are favored to meet design criteria; it also shows which positions in the sequence are readily changed and which positions are unlikely to change without disrupting protein stability and function. An experimental random library can be generated that is only randomized at the readily changeable, non-disruptive sequence positions. (2) The diversity of amino acids at these positions can be limited to those that the automated design shows are compatible with these positions. Thus, by limiting the number of randomized positions and the number of possibilities at these positions, the number of wasted sequences produced in the experimental library is reduced, thereby increasing the probability of success in finding sequences with useful properties.

For example, the table below lists the 10 favored sequences candidates from the virtual screening of 12 positions in a protein. It shows that positions 9, 10 and 12 are most likely to have changes that do not disrupt the function of the protein, suggesting that a random experimental library that randomizes positions 9, 10 and 12 will have a higher fraction of desirable sequences. Also, the virtual library suggests that position 10 is most compatible with Ile or Phe residues, further limiting the size of the library and allowing a more complete screening of good sequences.

in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme ($\beta$PKC), have been shown to block nuclear translocation of $\beta$PKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate bioactive agents as well.

|    | 1   | 2   | 3   | 4   | 5   | 6   | 7   | 8   | 9   | 10  | 11  | 12  |
|----|-----|-----|-----|-----|-----|-----|-----|-----|-----|-----|-----|-----|
| 1  | LEU | LEU | ILE | ILE | ALA | LEU | LEU | LEU | LEU | PHE | ALA | LEU |
| 2  | LEU | LEU | ILE | ILE | ALA | LEU | LEU | LEU | LEU | ILE | ALA | LEU |
| 3  | LEU | LEU | ILE | ILE | ALA | LEU | LEU | LEU | LEU | ILE | ALA | LEU |
| 4  | LEU | LEU | ILE | ILE | ALA | LEU | LEU | LEU | LEU | PHE | ALA | ILE |
| 5  | LEU | LEU | ILE | ILE | ALA | LEU | LEU | LEU | LEU | PHE | ALA | ILE |
| 6  | LEU | LEU | ILE | ILE | ALA | LEU | LEU | LEU | LEU | ILE | ALA | ILE |
| 7  | LEU | LEU | ILE | ILE | ALA | LEU | LEU | LEU | ILE | PHE | ALA | LEU |
| 8  | LEU | LEU | ILE | ILE | ALA | LEU | LEU | LEU | LEU | ILE | ALA | ILE |
| 9  | LEU | LEU | ILE | ILE | ALA | LEU | LEU | LEU | ILE | PHE | ALA | LEU |
| 10 | LEU | LEU | ILE | ILE | ALA | LEU | LEU | LEU | LEU | LEU | ALA | LEU |

The automated design method uses physical chemical criteria to screen sequences, resulting in sequences that are likely to be stable, structured, and that preserve function, if needed. Different design criteria can be used to produce candidate sets that are biased for properties such as charged, solubility, or active site characteristics (polarity, size), or are biased to have certain amino acids at certain positions. That is, The candidate bioactive agents and candidate nucleic acids are randomized, either fully randomized or they are biased in their randomization, e.g. in nucleotide/residue frequency generally or per position. By "randomized" or grammatical equivalents herein is meant that each nucleic acid and peptide consists of essentially random nucleotides and amino acids, respectively. Thus, any amino acid residue may be incorporated at any position. The synthetic process can be designed to generate randomized peptides and/or nucleic acids, to allow the formation of all or most of the possible combinations over the length of the nucleic acid, thus forming a library of randomized candidate nucleic acids.

In one embodiment, the library is fully randomized, with no sequence preferences or constants at any position. In a preferred embodiment, the library is biased. That is, some positions within the sequence are either held constant, or are selected from a limited number of possibilities. For example, In general, the generation of a prescreened random peptide libraries may be described as follows. Any structure, whether a known structure, for example a portion of a known protein, a known peptide, etc., or a synthetic structure, can be used as the backbone for PDA. For example, structures from X-ray crystallographic techniques, NMR techniques, de novo modelling, homology modelling, etc. may all be used to pick a backbone for which sequences are desired. Similarly, a number of molecules or protein domains are suitable as starting points for the generation of biased randomized candidate bioactive agents. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

Thus, in general, known peptide ligands can be used as the starting backbone for the generation of the primary library.

In addition, structures known to take on certain conformations may be used to create a backbone, and then sequences screened for those that are likely to take on that conformation. For example, there are a wide variety of "ministructures" known, sometimes referred to as "presentation structures", that can confer conformational stability or give a random sequence a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

Thus, synthetic presentation structures, i.e. artificial polypeptides, are capable of presenting a randomized peptide as a conformationally-restricted domain. Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference, and FIG. 3). Using this system investigators have isolated peptides capable of high affinity interaction with the appropriate target. In general, coiled-coil structures allow for between 6 to 20 randomized positions; (see Martin et al., EMBO J. 13(22):5303–5309 (1994), incorporated by reference).

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

Once the backbone is chosen and the primary library of the random peptides generated as outlined above, the secondary library generation and creation proceeds as for the known scaffold protein, including recombination of variant positions and/or amino acid residues, either computationally or experimentally. Again, libraries of DNA expressing the protein sequences defined by the automated protein design methods can be produced. Codons can be randomized at only the nucleotide sequence triplets that define the residue positions specified by the automated design method. Also, mixtures of base triplets that code for particular amino acids could be introduced into the DNA synthesis reaction to attach a full triplet defining an amino acid in one reaction step. Also, a library of random DNA oligomers could be designed that biases the desired positions toward certain amino acids, or that restricts those positions to certain amino acids. The amino acids biased for would be those specified in the virtual screening, or a subset of those.

Multiple DNA libraries are synthesized that code for different subsets of amino acids at certain positions, allowing generation of the amino acid diversity desired without having to fully randomize the codon and thereby waste sequences in the library on stop codons, frameshifts, undesired amino acids, etc. This can be done by creating a library that at each position to be randomized is only randomized at one or two of the positions of the triplet, where the position (s) left constant are those that the amino acids to be considered at this position have in common. Multiple DNA libraries would be created to insure that all amino acids desired at each position exist in the aggregate library.

Alternatively, the random peptide libraries may be done using the frequency tabulation and experimental generation methods including multiplexed PCR, shuffling, etc.

The present invention provides computer readable memories, central processing units, associated circuitry, and other associated compositions to implement the invention. The apparatus of the invention may include a central processing unit which communicates with a memory and a set of input/output devices (e.g., keyboard, mouse, monitor, printer, etc.) 26 through a bus. The general interaction between a central processing unit, a memory, input/output devices, and a bus is known in the art. The present invention is directed toward the automated protein design program and secondary library generator stored in the memory.

The automated protein design program and/or the secondary library generator may be implemented with a side chain module. As discussed in detail in the associated applications, the side chain module establishes a group of potential rotamers for a selected protein backbone structure. The protein design program may also be implemented with a ranking module. As discussed in detail below, the ranking module analyzes the interaction of rotamers with the protein backbone structure to generate optimized protein sequences. The protein design program may also include a search module to execute a search, for example a Monte Carlo search as described below, in relation to the optimized protein sequences. Finally, an assessment module may also be used to assess physical parameters associated with the derived proteins, as discussed further below.

The memory also stores a protein backbone structure, which is downloaded by a user through the input/output devices. The memory also stores information on potential rotamers derived by the side chain module. In addition, the memory stores protein sequences generated by the ranking module. The protein sequences may be passed as output to the input/output devices.

Using the nucleic acids of the present invention which encode library members, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the library protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the library protein, as will be appreciated by those in the art; for example, transcriptional and translational regulatory nucleic acid sequences from Bacillus are preferably used to express the library protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences include constitutive and inducible promoter sequences. The promoters may be either naturally occurring promoters, hybrid or synthetic promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors and appropriate selection and screening protocols are well known in the art and are described in e.g., Mansour et al., *Cell*, 51:503 (1988) and Murray, *Gene Transfer and Expression Protocols, Methods in Molecular Biology*, Vol. 7 (Clifton: Humana Press, 1991).

In addition, in a preferred embodiment, the expression vector contains a selection gene to allow the selection of transformed host cells containing the expression vector, and particularly in the case of mammalian cells, ensures the stability of the vector, since cells which do not contain the vector will generally die. Selection genes are well known in the art and will vary with the host cell used. By "selection gene" herein is meant any gene which encodes a gene product that confers resistance to a selection agent. Suitable selection agents include, but are not limited to, neomycin (or its analog G418), blasticidin S, histinidol D, bleomycin, puromycin, hygromycin B, and other drugs.

In a preferred embodiment, the expression vector contains a RNA splicing sequence upstream or downstream of the gene to be expressed in order to increase the level of gene expression. See Barret et al., Nucleic Acids Res. 1991; Groos et al., Mol. Cell. Biol. 1987; and Budiman et al., Mol. Cell. Biol. 1988.

A preferred expression vector system is a retroviral vector system such as is generally described in Mann et al., Cell, 33:153–9 (1993); Pear et al., Proc. Natl. Acad. Sci. U.S.A., 90(18):8392–6; Kitamura et al., Proc. Natl. Acad. Sci. U.S.A., 92:9146–50 (1995); Kinsella et al., Human Gene Therapy, 7:1405–13; Hofmann et al., Proc. Natl. Acad. Sci. U.S.A., 93:5185–90; Choate et al., Human Gene Therapy, 7:2247 (1996); PCT/US97/01019 and PCT/US97/01048, and references cited therein, all of which are hereby expressly incorporated by reference.

The library proteins of the present invention are produced by culturing a host cell transformed with nucleic acid, preferably an expression vector, containing nucleic acid encoding an library protein, under the appropriate conditions to induce or cause expression of the library protein. The conditions appropriate for library protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

As will be appreciated by those in the art, the type of cells used in the present invention can vary widely. Basically, a wide variety of appropriate host cells can be used, including yeast, bacteria, archaebacteria, fungi, and insect and animal cells, including mammalian cells. Of particular interest are *Drosophila melanogaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells. See the ATCC cell line catalog, hereby expressly incorporated by reference. In addition, the expression of the secondary libraries in phage display systems, such as are well known in the art, are particularly preferred, especially when the secondary library comprises random peptides. In one embodiment, the cells may be genetically engineered, that is, contain exogenous nucleic acid, for example, to contain target molecules.

In a preferred embodiment, the library proteins are expressed in mammalian cells. Any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a random library member. As is more fully described below, cell types implicated in a wide variety of disease conditions are particularly useful, so long as a suitable screen may be designed to allow the selection of cells that exhibit an altered phenotype as a consequence of the presence of a library member within the cell.

Accordingly, suitable mammalian cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepat6cytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

Mammalian expression systems are also known in the art, and include retroviral systems. A mammalian promoter is any DNA sequence capable of binding mammalian RNA polymerase and initiating the downstream (3') transcription of a coding sequence for library protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, library proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of library protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as , lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the library protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, library proteins are produced in insect cells. Expression vectors for the transformation of insect cells, and in particular, baculovirus-based expression vectors, are well known in the art and are described e.g., in O'Reilly et al., *Baculovirus Expression Vectors: A Laboratory Manual* (New York: Oxford University Press, 1994).

In a preferred embodiment, library protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The library protein may also be made as a fusion protein, using techniques well known in the art. Thus, for example, for the creation of monoclonal antibodies, if the desired epitope is small, the library protein may be fused to a carrier protein to form an immunogen. Alternatively, the library protein may be made as a fusion protein to increase expression, or for other reasons. For example, when the library protein is an library peptide, the nucleic acid encoding the peptide may be linked to other nucleic acid for expression purposes. Similarly, other fusion partners may be used, such as targeting sequences which allow the localization of the library members into a subcellular or extracellular compartment of the cell, rescue sequences or purification tags which allow the purification or isolation of either the library protein or the nucleic acids encoding them; stability sequences, which confer stability or protection from degradation to the library protein or the nucleic acid encoding it, for example resistance to proteolytic degradation, or combinations of these, as well as linker sequences as needed.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signaling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the library member comprises a rescue sequence. A rescue sequence is a sequence which may be used to purify or isolate either the candidate agent or the nucleic acid encoding it. Thus, for example, peptide rescue sequences include purification sequences such as the $His_6$ tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the library member or the nucleic acid encoding it. Thus, for example, peptides may be stabilized by the incorporation of glycines after the initiation methionine (MG or MGGG), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: $MG(X)_nGGPP$, where X is any amino acid and n is an integer of at least four.

In one embodiment, the library nucleic acids, proteins and antibodies of the invention are labeled. By "labeled" herein is meant that nucleic acids, proteins and antibodies of the invention have at least one element, isotope or chemical compound attached to enable the detection of nucleic acids, proteins and antibodies of the invention. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the library protein is purified or isolated after expression. Library proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the library protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the library protein. In some instances no purification will be necessary.

Once expressed and purified if necessary, the library proteins and nucleic acids are useful in a number of applications.

In general, the secondary libraries are screened for biological activity. These screens will be based on the scaffold protein chosen, as is known in the art. Thus, any number of protein activities or attributes may be tested, including its binding to its known binding members (for example, its substrates, if it is an enzyme), activity profiles, stability profiles (pH, thermal, buffer conditions), substrate specificity, immunogenicity, toxicity, etc.

When random peptides are made, these may be used in a variety of ways to screen for activity. In a preferred embodiment, a first plurality of cells is screened. That is, the cells into which the library member nucleic acids are introduced are screened-for an altered phenotype. Thus, in this embodiment, the effect of the library member is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the secondary library, i.e. a different library member, although as will be appreciated by those in the art, some cells within the library may not contain one and some may contain more than one. When methods other than retroviral infection are used to introduce the library members into a plurality of cells, the distribution of library members within the individual cell members of the cellular library may vary widely, as it is generally difficult to control the number of nucleic acids which enter a cell during electroporation, etc.

In a preferred embodiment, the library nucleic acids are introduced into a first plurality of cells, and the effect of the library members is screened in a second or third plurality of cells, different from the first plurality of cells, i.e. generally a different cell type. That is, the effect of the library member is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the library members (for example, when inducible promoters are used), to produce the library proteins.

Thus, in one embodiment, the methods of the present invention comprise introducing a molecular library of library members into a plurality of cells, a cellular library. The plurality of cells is then screened, as is more fully outlined below, for a cell exhibiting an altered phenotype. The altered phenotype is due to the presence of a library member.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the library member can change the phenotype of the cell in some detectable and/or measurable way.

The altered phenotype may be detected in a wide variety of ways, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the randomized nucleic acid was introduced; in other embodiments, the altered phenotype is detected in a second cell which is responding to some molecular signal from the first cell.

In a preferred embodiment, the library member is isolated from the positive cell. This may be done in a number of ways. In a preferred embodiment, primers complementary to DNA regions common to the constructs, or to specific components of the library such as a rescue sequence, defined above, are used to "rescue" the unique random sequence. Alternatively, the member is isolated using a rescue sequence. Thus, for example, rescue sequences comprising epitope tags or purification sequences may be used to pull out the library member, using immunoprecipitation or affinity columns. In some instances, this may also pull out things to which the library member binds (for example the primary target molecule) if there is a sufficiently strong binding interaction between the library member and the target molecule. Alternatively, the peptide may be detected using mass spectroscopy.

Once rescued, the sequence of the library member is determined. This information can then be used in a number of ways.

In a preferred embodiment, the member is resynthesized and reintroduced into the target cells, to 1 0 verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of the member is used to generate more libraries, as outlined herein.

In a preferred embodiment, the library member is used to identify target molecules, i.e. the molecules with which the member interacts. As will be appreciated by those in the art, there may be primary target molecules, to which the library member binds or acts upon directly, and there may be secondary target molecules, which are part of the signaling pathway affected by the library member; these might be termed "validated targets".

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable library member is found, the undesirable effect may be reduced or eliminated. Alternatively, normally desirable consequences may be reduced or eliminated, with an eye towards elucidating the cellular mechanisms associated with the disease state or signaling pathway.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Computational Prescreening on β-lactamase TEM-1

Preliminary experiments were performed on the β-lactamase gene TEM-1. Brookhaven Protein Data Bank entry 1 BTL was used as the starting structure. All water molecules and the $SO_4^{2-}$ group were removed and explicit hydrogens were generated on the structure. The structure was then minimized for 50 steps without electrostatics using the conjugate gradient method and the Dreiding II force field. These steps were performed using the BIOGRAF program (Molecular Simulations, Inc., San Diego, Calif.). This minimized structure served as the template for all the protein design calculations.

Computational Pre-screening

Computational pre-screening of sequences was performed using PDA. A 4 Å sphere was drawn around the heavy side chain atoms of the four catalytic residues (S70, K73, S130, and E166) and all amino acids having heavy side chain atoms within this distance cutoff were selected. This yielded the following 7 positions: F72, Y105, N132, N136, L169, N170, and K234. Two of these residues, N132 and K234, are highly conserved across several different β-lactamases and were therefore not included in the design, leaving five variable positions (F72, Y105, N136, L169, N170). These designed positions were allowed to change their identity to any of the 20 naturally occurring amino acids except proline, cysteine, and glycine (a total of 17 amino acids). Proline is usually not allowed since it is difficult to define appropriate rotamers for proline, cysteine is excluded to prevent formation of disulfide bonds, and glycine is excluded because of conformational flexibility.

Additionally, a second set of residues within 5 Å of the residues selected for PDA design were floated (their amino acid identity was retained as wild type, but their conformation was allowed to change). The heavy side chain atoms were again used to determine which residues were within the cutoff. This yielded the following 28 positions: M68, M69, S70, T71, K73, V74, L76, V103, E104, S106, P107, I127, M129, S130, A135, L139, L148, L162, R164, W165, E166, P167, D179, M211, D214, V216, S235, I247. A248 was included as a floated position instead of I247. The two prolines, P107 and P167, were excluded from the floated residues, as were positions M69, R164, and W165, since their crystal structures exhibit highly strained rotamers, leaving 23 floated residues from the second set. The conserved residues N132 and K234 from the first sphere (4 Å) were also floated, resulting in a total of 25 floated residues.

The potential functions and parameters used in the PDA calculations were as follows. The van der Waals scale factor was set to 0.9, and the electrostatic potential was calculated using a distance attenuation and a dielectric constant of 40. The well depth for the hydrogen bond potential was set to 8 kcal/mol with a local and remote backbone scale factor of 0.25 and 1.0 respectively. The solvation potential was only calculated for designed positions classified as core (F72, L169, M68, T71, V74, L76, I127, A135, L139, L148, L162, M211 and A248). Type 2 solvation was used (Street and Mayo, 1998). The non-polar exposure multiplication factor was set to 1.6, the non-polar burial energy was set to 0.048 kcal/mol/$A^2$, and the polar hydrogen burial energy was set to 2.0 kcal/mol.

The Dead End Elimination (DEE) optimization method (see reference) was used to find the lowest energy, ground state sequence. DEE cutoffs of 50 and 100 kcal/mol were used for singles and doubles energy calculations, respectively.

Starting from the DEE ground state sequence, a Monte Carlo (MC) calculation was performed that generated a list of the 1000 lowest energy sequences. The MC parameters were 100 annealing cycles with 1,000,000 steps per cycle. The non-productive cycle limit was set to 50. In the annealing schedule, the high and low temperatures were set to 5000 and 100 K respectively.

The following probability distribution was then calculated from the top 1000 sequences in the MC list (see Table 3 below). It shows the number of occurrences of each of the amino acids selected for each position (the 5 variable positions and the 25 floated positions).

TABLE 3

Monte Carlo analysis (amino acids and their number of occurrences (for the top 1000 sequences)

| Position | Amino acid occurrences |
| --- | --- |
| 68 | M:1000 |
| 70 | S:1000 |
| 71 | T:1000 |
| 72 | Y:591 F:365 V: 35 E: 8 L: 1 |
| 73 | K:1000 |
| 74 | V:1000 |
| 76 | L:1000 |
| 103 | V:1000 |
| 104 | E:1000 |
| 105 | M:183 Q:142 I:132 N:129 E:126 S:115 D:97 A:76 |
| 106 | S:1000 |
| 127 | I:1000 |
| 129 | M:1000 |
| 130 | S:1000 |
| 132 | N:1000 |
| 135 | A:1000 |
| 136 | D:530 M:135 N: 97 V: 68 E: 66 S:38 T:33 A:27 Q:6 |
| 139 | L:1000 |
| 148 | L:1000 |
| 162 | L:1000 |
| 166 | E:1000 |
| 169 | L:689 E:156 M:64 S:37 D:23 A:21 Q:10 |
| 170 | M:249 L:118 E:113 D:112 T:90 Q:87 S:66 R:44 A:35 N:24 F:21 K:15 Y:9 H:9 V:8 |
| 179 | D:1000 |
| 211 | M:1000 |
| 214 | D:1000 |
| 216 | V:1000 |
| 234 | K:1000 |
| 235 | S:1000 |

This probability distribution was then transformed into a rounded probability distribution (see Table 4). A 10% cutoff value was used to round at the designed positions and the wild type amino acids were forced to occur with a probability of at least 10%. An E was found at position 169 15.6% of the time. However, since this position is adjacent to another designed position,170, its closeness would have required a more complicated oligonucleotide library design; E was therefore not included for this position when generating th sequence library (only L was used).

TABLE 4

PDA probability distribution for the designed positions of β-lactamase (rounded to the nearest 10%).

| 72 | 105 | 136 | 169 | 170 |
| --- | --- | --- | --- | --- |
| Y 50% | M 20% | D 70% | L 100% | M 30% |
| F 50% | Q 20% | M 20% | | L 20% |
| | I 20% | N 10% | | E 20% |
| | N 10% | | | D 20% |
| | E 10% | | | N 10% |
| | S 10% | | | |
| | Y 10% | | | |

As seen from Table 4, the computational pre-screening resulted in an enormous reduction in the size of the problem. Originally, 17 different amino acids were allowed at each of the 5 designed positions, giving $17^5$=1,419,857 possible sequences. This was pared down to just 2*7*3*1*5=210 possible sequences—a reduction of nearly four orders of magnitude.

Generation of Sequence Library

Overlapping oligonucleotides corresponding to the full length TEM-1 gene for β-lacatamaseand all desired mutationswere synthesized and used in a PCR reaction as described previously (FIG. 1), resulting in a sequence library containing the 210 sequences described above.

Synthesis of Mutant TEM-1 genes

To allow the mutation of the TEM-1 gene, pCR2.1 (Invitrogen) was digested with Xbal and EcoRI, blunt ended with T4 DNA polymerase, and religated. This removes the HindIII and XhoI sites within the polylinker. A new XhoI site was then introduced into the TEM-1 gene at position 2269 (numbering as of the original pCR2.1) using a Quickchange Site-Directed Mutagenesis Kit as described by the manufacturer (Stratagene). Similarly, a new HindIII site was introduced at position 2674 to give pCR-Xen1.

To construct the mutated TEM-1 genes, overlapping 40mer oligonucleotides were synthesized corresponding to the sequence between the newly introduced Xho1 and HindIII sites, designed to allow a 20 nucleotide overlap with adjacent oligonucleotides. At each of the designed positions (72, 105, 136 and 170) multiple oligonucleotides were synthesized, each containing a different mutation so that all the possible combinations of mutant sequences (210) could be made in the desired proportions as shown in Table 4. For example, at position 72, two sets of oligonucleotideswere synthesized, one containing an F at position 72, the other containing a Y. Each oligonucleotide was resuspended at a concentration of 1 μg/μl, and equal molar concentrations of the oligonucleotides were pooled.

At the redundant positions, each oligonucleotide was added at a concentration that reflected the probabilities in Table 4. For example, at position 72 equal amounts of the two oligonucleotides were added to the pool, while at position 136, twice as much M-containing oligonucleotide was added compared to the N-containing oligonucleotide, and seven times as much D-containing oligonucleotide was added compared to the N-containing oligonucleotide.

DNA Library Assembly

For the first round of PCR, 2 µl of pooled oligonucleotides at the desired probabilities (Table4) were added 30 to a 100 µl reaction that contained 2 µl 10 mM dNTPs, 10 µl 10×Taq buffer (Qiagen), 1 µl of Taq DNA polymerase(5 units/µl: Qiagen) and 2 µl Pfu DNA polymerase (2.5 units/µl: Promega). The reaction mixture was assembled on ice and subjected to 94° C. for 5 minutes, 15 cycles of 94° C. for 30 seconds, 52° C. 30 seconds and 72° C. for 30 seconds, and a final extension step of 72° C. for 10 minutes.

Isolation of Full Length Oligonucleotides

For the second round of PCR, 2.5 µl of the first round reaction was added to a 100 µl reaction containing 2 µl 110 mM dNTPs, 10 µl of 10×Pfu DNA polymerase buffer (Promega), 2 µl Pfu DNA polymerase (2.5 units/µl: Promega), and 1 µg of oligonucleotides corresponding to the 5' and 3' ends of the synthesized gene. The reaction mixture was assembled on ice and subjected to 94° C. for 5 minutes, 20 cycles of 94°C. for 30 seconds, 52° C. for 30 seconds and 72° C. for 30 seconds, and a final extension step of 72 minutes to isolate the full length oligonucleotides.

Purification of DNA Library

The PCR products were purified using a QIAquick PCR Purification Kit (Qiagen), digested with Xho1 and HindIII, electrophoresed through a 1.2% agarose gel and re-purified using a QIAquick Gel Extraction Kit (Qiagen).

Verification of Sequence Library Identity

The PCR products containing the library of mutant TEM-1 β-lactamase genes were then cloned between a promoter and terminator in a kanamycin resistant plasmid and transformed into $E\ coli$. An equal number of bacteria were then spread onto media containing either kanamycin or ampicillin. All transformed colonies will be resistant to kanamycin, but only those with active mutated β-lactamasegenes will grow on ampicillin After overnight incubation, several colonies were observed on both plates, indicating that at least one of the above sequences encodes an active Pβ-lactamase. The number of colonies on the kanamycin plate far outnumbered those on the ampicillin plate (roughly a 5:1 ratio) suggesting that either some of the sequences destroy activity, or that the PCR introduces errors that yield an inactive or truncated enzyme.

To distinguish between these possibilities, 60 colonies were picked from the kanamycin plate and their plasmid DNA was sequenced. This gave the distribution shown in Table 5.

This small test demonstrates that multiple PCR with pooled oligonucleotides can be used to construct a sequence library that reflects the desired proportions of amino acid changes.

Experimental Screening of Sequence Library

The purified PCR product containing the library of mutated sequences was then ligated into pCR-Xen1 that had previously been digested with Xho1 and HindIII and purified. The ligation reaction was transformed into competent TOP10 $E.\ coli$ cells (Invitrogen). After allowing the cells to recover for 1 hour at 37° C., the cells were spread onto LB plates containing the antibiotic cefotaxime at concentrations ranging from 0.1 µg/ml to 50 µg/ml and selected for increasing resistance.

A triple mutant was found that improved enzyme function by 35 fold in only a single round of screening (see FIG. 4). This mutant (Y105Q, N136D, N170L) survived at 50 µg/ml cefotaxime.

Example 2

Secondary Library generation of a Xylanase

PDA Pre-screening Leads to Enormous Reduction in Number of Possible Sequences

To demonstrate that computational pre-screening is feasible and will lead to a significant reduction in the number of sequences that have to be experimentally screened, initial calculations for the $B.\ circulans$ xylanase with and without the substrate were performed. The PDB structure 1XNB of $B.\ circulans$ xylanase and 1BCX for the enzyme substrate complex were used. 27 residues inside the binding site were visually identified as belonging to the active site. 8 of these residues were regarded as absolutely essential for the enzymatic activity. These positions were treated as wild type residues, which means that their conformation was allowed to change but not their amino acid identity (see FIG. 2).

Three of the 20 naturally occurring amino acids were not considered (cysteine, proline, and glycine). Therefore, 17 different amino acids were still possible at the remaining 19 positions; the problem yields $17^{19}=2.4 \times 10^{23}$ different amino acid sequences. This number is 10 orders of magnitude larger than what can be handled by state of the art directed evolution methods. Clearly these approaches cannot be used to screen the complete dimensionality of the problem and consider all sequences with multiple substitutions. Therefore PDA calculations were performed to reduce the search space. A list of the 10,000 lowest energy sequences was created and the probability for each amino acid at each position was determined (see Table 1).

TABLE 5

Percentages predicted by PDA vs. those observed from experiment for the designed positions.

| Wild Type | PDA Residues (Predicted Percentage/Observed Percentage) | | | | | |
|---|---|---|---|---|---|---|
| 72F | Y 50/50 | F 50/50 | | | | |
| 105Y | M 20/27 | Q 20/18 | I 20/21 | N 10/7 | E 10/7 | S 10/10 Y 10/10 |
| 136N | D 70/72 | M 20/17 | N 10/11 | | | |
| 170N | M 30/34 | L 20/21 | E 20/21 | D 20/17 | N 10/7 | |

Note that the observed percentages of each amino acid at all four positions closely match the predicted percentages. Sequencing also revealed that only one of the 60 colonies contained a PCR error, a G to C transition.

TABLE 1

Probability of amino acids at the designed positions resulting from the PDA calculation of the wild type (WT) enzyme structure. Only amino acids with a probability greater than 1% are shown.

| WT | PDA Probability Distribution | | | | | | |
|---|---|---|---|---|---|---|---|
| 5 Y | W 37.2% | F 25.8% | Y 22.9% | H 14.0% | | | |
| 7 Q | E 69.1% | L 30.2% | | | | | |
| 11 D | I 41.2% | D 10.7% | V 10.1% | M 7.9% | L 6.4% | E 5.3% | T 4.2% |
| | Q 3.8% | Y 2.6% | F 2.1% | N 1.9% | S 1.9% | A 1.1% | |
| 37 V | D 29.9% | M 29.4% | V 21.4% | S 12.8% | I 4.1% | E 1.0% | |
| 39 G | A 99.8% | | | | | | |
| 63 N | W 91.2% | Q 6.7% | A 1.4% | | | | |
| 65 Y | E 91.7% | L 4.9% | M 3.4% | | | | |
| 67 T | E 81.0% | D 12.3% | L 3.9% | A 1.7% | | | |
| 71 W | V 37.8% | F 25.5% | W 8.5% | M 6.0% | D 5.8% | E 4.3% | I 1.0% |
| 80 Y | M 32.4% | L 31.5% | F 19.0% | I 5.9% | Y 5.7% | E 3.7% | |
| 82 V | V 88.6% | D 11.0% | | | | | |
| 88 Y | N 91.1% | K 6.6% | W 1.3% | | | | |
| 110 T | D 99.9% | | | | | | |
| 115 A | A 35.6% | Y 27.8% | T 14.4% | D 10.2% | S 9.2% | F 2.6% | |
| 118 E | E 92.2% | D 2.6% | I 2.0% | A 1.7% | | | |
| 125 F | F 79.4% | Y 11.8% | M 7.3% | L 1.5% | | | |
| 129 W | E 91.3% | S 8.6% | | | | | |
| 168 V | D 98.1% | A 1.0% | | | | | |
| 170 A | A 78.7% | S 17.6% | D 3.7% | | | | |

If we consider all the amino acids obtained from the PDA calculation, including those with probabilities less than 1%, we obtain $4.1 \times 10^{15}$ different amino acid sequences. This is a reduction by 7 orders of magnitude. If one only considers those amino acids that have at least a probability of more than 1% as shown in Table 1 (1% criterion), the problem is decreased to $3.3 \times 10^9$ sequences. If one neglects all amino acids with a probability of less than 5% (5% criterion) there are only $4.0 \times 10^6$ sequences left. This is a number that can be easily handled by screening and gene shuffling techniques. Increasing the list of low energy sequences to 100,000 does not change these numbers significantly and the effect on the amino acids obtained at each position is negligible. Changes occur only among the amino acids with a probability of less than 1%.

Including the substrate in the PDA calculation further reduced the number of amino acids found at each position. If we consider those amino acids with a probability higher than 5%, we obtain $2.4 \times 10^6$ sequences (see Table 2).

TABLE 2

Probability of amino acids at the designed positions resulting from the PDA calculation of the enzyme substrate complex. Only those amino acids with a probability greater than 1% are shown.

| WT | PDA Probability Distribution | | | | | | |
|---|---|---|---|---|---|---|---|
| 5 Y | Y 69.2% | W 17.0% | H 7.3% | F 6.0% | | | |
| 7 Q | Q 78.1% | E 18.0% | L 3.9% | | | | |
| 11 D | D 97.1% | | | | | | |
| 37 V | V 50.9% | D 33.9% | S 5.4% | A 1.2% | L 1.0% | | |
| 39 G | S 80.6% | A 19.4% | | | | | |
| 63 N | W 92.2% | D 3.9% | Q 2.9% | | | | |
| 65 Y | E 91.1% | L 8.7% | | | | | |
| 67 T | E 92.8% | L 5.2% | | | | | |
| 71 W | W 62.6% | E 13.3% | M 11.0% | S 6.9% | D 4.0% | | |
| 80 Y | M 66.4% | F 13.6% | E 10.7% | I 6.0% | L 1.3% | | |
| 82 V | V 86.0% | D 12.8% | | | | | |
| 88 Y | W 55.1% | Y 15.9% | N 11.4% | F 9.5% | K 1.9% | Q 1.4% | D 1.4% |
| | | | | | | | M 1.4% |
| 110 T | D 99.9% | | | | | | |
| 115 A | D 46.1% | S 27.8% | T 17.1% | A 7.9% | | | |
| 118 E | I 47.6% | D 43.0% | E 3.6% | V 2.5% | A 1.4% | | |
| 125 F | Y 51.1% | F 43.3% | L 3.4% | M 2.0% | | | |
| 129 W | L 63.2% | M 28.1% | E 7.5% | | | | |
| 168 V | D 98.2% | | | | | | |
| 170 A | T 92.3% | A 5.9% | | | | | |

These preliminary calculations show that PDA can significantly reduce the dimensionality of the problem and can bring it into the scope of gene shuffling and screening techniques (see FIG. 3).

We claim:

1. A method for generating a secondary library of scaffold protein variants comprising:
   a) providing a primary library comprising a computationally rank-ordered list of scaffold protein primary variant sequences;

b) generating a list of primary variant positions in said primary library;

c) combining a plurality of said primary variant positions to generate a secondary library of secondary sequences.

2. A method for generating a secondary library of scaffold protein variants comprising:

a) providing a primary library comprising a computationally rank-ordered list of scaffold protein primary variant sequences comprising primary variant positions; and, b) combining a plurality of said primary variant positions to generate a secondary library of secondary sequences.

3. A method for generating a secondary library of scaffold protein variants comprising:

a) providing a primary library comprising a computationally rank-ordered list of scaffold protein primary variant sequences;

b) generating a probability distribution table of amino acid residues in a plurality of variant positions;

c) combining a plurality of said amino acid residues to generate a secondary library of secondary sequences.

4. A method for generating a secondary library of scaffold protein variants comprising:

a) providing a first library computationally rank-ordered list of scaffold protein primary variants;

b) generating a probability distribution of amino acid residues in a plurality of variant positions;

c) synthesizing a plurality of scaffold protein secondary variants comprising a plurality of said amino acid residues to forma secondary library;

wherein at least one of said secondary variants is different from said primary variants.

5. A method according to claim 1, 2, 3, or 4 further comprising synthesizing a plurality of said secondary sequences.

6. A method according to claim 5 wherein said synthesizing is done by multiple PCR with pooled oligonucleotides.

7. A method according to claim 6 wherein said pooled oligonucleotides are added in equimolar amounts.

8. A method according to claim 5 wherein said pooled oligonucleotides are added in amounts that correspond to the frequency of the mutation.

\* \* \* \* \*

UNITED STATES PATENT AND TRADEMARK OFFICE
CERTIFICATE OF CORRECTION

PATENT NO. : 6,403,312 B1
DATED : June 11, 2002
INVENTOR(S) : Bassil I. Dahiyat et al.

It is certified that error appears in the above-identified patent and that said Letters Patent is hereby corrected as shown below:

Title page,
Item [54], change "AUTOMATIC" to -- AUTOMATION --.
Item [57], ABSTRACT, change "automaton" to -- automation --.

Column 2,
Line 17, change "error prone" to -- error-prone --.
Lines 27 and 28, after "variants" delete ";" and insert paragraph beginning at line 28 through line 33.
Line 47, change "Van" to -- van --.
Line 49, change "salvation" to -- solvation --.
Lines 53 and 54, change "rank ordered" to -- rank-ordered --.
Line 67, change "Pfu" to -- *Pfu* --.

Column 4,
Line 2, change "examples" to -- example --.
Line 8, change "T cells" to -- T-cells --.

Column 5,
Line 24, correct spelling in both occurrences of "occuring" to -- occurring --
Line 32, change "three dimensional" to -- three-dimensional --.
Line 35, correct spelling in both occurrences of "modelling" to -- modeling --.
Line 40, change "extremeophiles" to -- extremophiles --; and change "archebacteria" to -- archabacteria --.

Column 6,
Lines 7 and 8, change "Granulocyte-Macrophage" to -- Granulocyte--.
Line 29, change "coaguation" to -- coagulation --.
Line 31, change "Zn fingers" to -- zinc fingers --.
Line 38, change "Pleckstin" to -- Pleckstrin --.
Lines 44 and 45, change "T Cell" to -- T-Cell --.
Line 67, change "rank ordered" to -- rank-ordered --.

Column 7,
Line 2, change "top 1" to -- top $10^5$ --.
Line 52, change "rank ordered" to -- rank-ordered --.

Column 9,
Line 46, change "occuring" to -- occurring --.

UNITED STATES PATENT AND TRADEMARK OFFICE
CERTIFICATE OF CORRECTION

PATENT NO. : 6,403,312 B1
DATED : June 11, 2002
INVENTOR(S) : Bassil I. Dahiyat et al.

It is certified that error appears in the above-identified patent and that said Letters Patent is hereby corrected as shown below:

<u>Column 10,</u>
Line 1, change "it's" to -- its --.
Line 4, change "occuring" to -- occurring --.
Lines 18 and 19, change "three dimensional" to -- three-dimensional --.
Line 46, change "metal binding" to -- metal-binding --.

<u>Column 11,</u>
Line 5, change "modelling" to -- modeling --.
Line 22, change "a" to -- α --.
Line 34, change "lysine" to -- lysine, --.
Line 40, change "occuring" to -- occurring --.

<u>Column 12,</u>
Line 9, change "Van" to -- van --.
Line 41, delete "10".

<u>Column 13,</u>
Line 40, change "7,926," to -- 09/127,926 --.

<u>Column 14,</u>
Line 28, 33, 34 and 38, change "rank ordered" to -- rank-ordered --.

<u>Column 16,</u>
Line 15, change "rank order" to -- rank-ordered --.
Line 65, change "full length" to -- full-length --.

<u>Column 17,</u>
Lines 3 and 8, change "full length" to -- full-length --.
Line 45, change "Error prone" to -- Error-prone --.

<u>Column 18,</u>
Line 13, change "error prone" to -- error-prone --.

<u>Column 19,</u>
Line 21, change "sequences" to -- sequence --.
Line 51, change "The candidate" to -- the candidate --.

UNITED STATES PATENT AND TRADEMARK OFFICE
CERTIFICATE OF CORRECTION

PATENT NO. : 6,403,312 B1
DATED : June 11, 2002
INVENTOR(S) : Bassil I. Dahiyat et al.

It is certified that error appears in the above-identified patent and that said Letters Patent is hereby corrected as shown below:

Column 20,
Lines 17 and 20, change "Xenopus" to -- *Xenopus* --.
Line 18, change "anti-tumour" to -- anti-tumor --.
Line 50, change "modelling" to -- modeling --.

Column 21,
Line 6, change "structures"," to -- structures," --.
Line 12, change "side-chain" to -- side chain --.
Line 13, change "Therefore" to -- Therefore, --.
Line 29, change "zinc-finger" to -- zinc finger --.
Line 44, after "complementarily" insert -- determining --.

Column 23,
Lines 14 and 15, change "Bacillus" to -- *Bacillus* --.

Column 24,
Line 9, change "an library" to -- a library --.
Line 28, change "Neurospora" to -- *Neurospora* --.

Column 25,
Line 8, change "using a" to -- usually --.

Column 26,
Line 58, change "to the" to -- of the --.

Column 27,
Line 63, change "purified" to -- purified, --.

Column 28,
Line 10, change "screened-for" to -- screened for --.

Column 29,
Line 6, change "susceptability," to -- susceptibility --.
Line 46, delete "1 0".

Column 30,
Lines 30 and 31, add a line space after "calculations" and after "Computational Pre-screening".
Line 57, change "of 1247" to -- I247 --.
Line 62, change "25" to -- 25 --.

UNITED STATES PATENT AND TRADEMARK OFFICE
CERTIFICATE OF CORRECTION

PATENT NO. : 6,403,312 B1
DATED : June 11, 2002
INVENTOR(S) : Bassil I. Dahiyat et al.

It is certified that error appears in the above-identified patent and that said Letters Patent is hereby corrected as shown below:

Column 31,
In TABLE 3, at lines 30 and 31, change "Posi-" to -- Position Amino acid occurrences --.
In TABLE 3, at line 57 below "235 S:1000" add -- 248 A:1000 --.

Column 32,
Line 28, change "β-lacatamase" to -- β-lactamase --.
Lines 38 and 47, change "XhoI" to -- XhoI --.

Column 33,
Line 1, after "Assembly" add a line space.
Line 3, change "(Table4)" to -- (Table 4) -- and delete "30".
Line 5, change "polymerase(5" to -- polymerase (5 --.
Line 6, change "Pfu" to -- *Pfu* --.
Lines 8, 9 and 10, in all occurrences change "C." to -- C --.
Line 10, after "minutes." add a line space.
Line 11, after "Oligonucleotides" add a line space.
Line 12, change "2 μl 110" to -- 2 μl 10 --.
Line 13, change "10xPfu" to -- 10x*Pfu* --.
Line 14, change "Pfu" to -- *Pfu* --.
Lines 17, 18 and 19, in all occurrences change "C." to -- C --.
Line 20, after "oligonucleotides." add a line space.
Line 21, after "Library" add a line space.
Line 23, change "XhoI" to -- XhoI --.
Line 25, after "(Qiagen)." add a line space.
Line 26, after "Identity" add a line space.
Line 34, change " β-lactamasegenes" to -- β-lactamase genes -- and insert a -- . -- after "ampicillin".
Line 37, change "Pβ-lactamase" to -- β-lactamase --.

UNITED STATES PATENT AND TRADEMARK OFFICE
CERTIFICATE OF CORRECTION

PATENT NO.    : 6,403,312 B1
DATED         : June 11, 2002
INVENTOR(S)   : Bassil I. Dahiyat et al.

It is certified that error appears in the above-identified patent and that said Letters Patent is hereby corrected as shown below:

<u>Column 34,</u>
Line 4, after "changes." add a line space.
Line 5, after "Library" add a line space.
Line 8, change "Xhol" to -- XhoI --.
Line 11, change "C." to -- C --.
Line 15, change "35 fold" to -- 35-fold --.
Line 20, after "Xylanase" add a line space.
Line 22, after "Sequences" add a line space.

<u>Column 38,</u>
Line 8, change "forma" to -- form a --.

Signed and Sealed this

Eighth Day of July, 2003

JAMES E. ROGAN
*Director of the United States Patent and Trademark Office*